US009816051B2

(12) United States Patent
Wels et al.

(10) Patent No.: US 9,816,051 B2
(45) Date of Patent: Nov. 14, 2017

(54) METATHESIS OF OLEFINS USING RUTHENIUM BASED CATALYTIC COMPLEXES

(71) Applicant: CRODA INTERNATIONAL PLC, Yorkshire (GB)

(72) Inventors: Bastiaan Wels, Utrecht (NL); Hans Ridderikhoff, Gouda (NL); Tanja Van Bergen-Brenkman, Gouda (NL); Dessy Liminto, The Hague (NL)

(73) Assignee: Croda International PLC, East Yorkshire (GB)

(*) Notice: Subject to any disclaimer, the term of this patent is extended or adjusted under 35 U.S.C. 154(b) by 0 days.

(21) Appl. No.: 14/383,329

(22) PCT Filed: Mar. 18, 2013

(86) PCT No.: PCT/GB2013/050684
§ 371 (c)(1),
(2) Date: Sep. 5, 2014

(87) PCT Pub. No.: WO2013/140144
PCT Pub. Date: Sep. 26, 2013

(65) Prior Publication Data
US 2015/0018574 A1    Jan. 15, 2015

(30) Foreign Application Priority Data
Mar. 18, 2012 (GB) .................................. 1204715.5

(51) Int. Cl.
| C07C 67/27 | (2006.01) |
| C07C 51/373 | (2006.01) |
| C11C 3/00 | (2006.01) |
| C07C 6/04 | (2006.01) |
| C07C 6/02 | (2006.01) |
| B01J 31/12 | (2006.01) |
| B01J 31/14 | (2006.01) |
| B01J 31/22 | (2006.01) |
| C07C 1/213 | (2006.01) |
| C07C 67/475 | (2006.01) |

(52) U.S. Cl.
CPC ............... *C11C 3/00* (2013.01); *B01J 31/128* (2013.01); *B01J 31/146* (2013.01); *B01J 31/2273* (2013.01); *B01J 31/2278* (2013.01); *C07C 1/213* (2013.01); *C07C 6/02* (2013.01); *C07C 6/04* (2013.01); *C07C 51/373* (2013.01); *C07C 67/27* (2013.01); *C07C 67/475* (2013.01); *B01J 2231/54* (2013.01); *B01J 2531/821* (2013.01); *C07C 2527/135* (2013.01); *C07C 2531/12* (2013.01); *C07C 2531/22* (2013.01); *C07C 2531/30* (2013.01); *C10G 2300/1014* (2013.01)

(58) Field of Classification Search
CPC ..... C07C 67/27; C07C 51/373; C07C 2531/30
USPC .................................................. 560/202, 595
See application file for complete search history.

(56) References Cited

U.S. PATENT DOCUMENTS

| 4,654,462 | A | 3/1987 | Basset et al. |
| 4,943,397 | A | 7/1990 | Johnson |
| 5,312,940 | A | 5/1994 | Grubbs et al. |
| 6,388,032 | B1 | 5/2002 | Yamaura et al. |
| 6,861,386 | B2 | 3/2005 | Angeletakis et al. |
| 8,288,558 | B2 | 10/2012 | Arlt et al. |
| 8,394,965 | B2 | 3/2013 | Mauduit et al. |
| 9,120,736 | B2 | 9/2015 | Gooβen et al. |
| 2003/0023123 | A1 | 1/2003 | Paulson et al. |
| 2005/0043541 | A1 | 2/2005 | Walter et al. |
| 2006/0211905 | A1* | 9/2006 | Forman ..................... C07C 6/04 585/645 |
| 2007/0112158 | A1 | 5/2007 | Hayakawa et al. |
| 2009/0069516 | A1 | 3/2009 | Obrecht et al. |
| 2010/0022789 | A1 | 1/2010 | Mignani et al. |
| 2010/0087644 | A1* | 4/2010 | Mauduit et al. ................ 546/4 |
| 2011/0160472 | A1* | 6/2011 | Lemke et al. ................ 554/154 |
| 2011/0171147 | A1* | 7/2011 | Samorski .............. C07C 67/475 424/59 |

FOREIGN PATENT DOCUMENTS

| WO | 9320111 | 10/1993 |
| WO | 9604289 | 2/1996 |
| WO | WO 00/15339 | 3/2000 |
| WO | WO 02/14376 | 2/2002 |
| WO | 02076920 A1 | 10/2002 |
| WO | WO 03/062253 | 7/2003 |
| WO | 2004037754 A2 | 5/2004 |
| WO | WO 2007/010453 | 1/2007 |

(Continued)

OTHER PUBLICATIONS

Fujimura et al. J. Org. Chem. (1994), V59, p. 4029-4031.*
Thomas et al. Int. J. Mol. Sci. (2009), V.10, p. 5020-5030.*
Thomas et al. Int. J. Mol. Sci. (2011), V.12, p. 3989-3997.*
Anonymous Third Party Observation for PCT/GB2013/050684, submitted Jul. 17, 2014.
Fürstner, Alois; Thiel, Oliver R.; Lehmann, Christian W.; "Study Concerning the Effects of Chelation on the Structure and Catalytic Activity of Ruthenium Carbene Complexes"; Organometallics 2002, vol. 21, pp. 331-335.
Grela, Karol; Harutyunyan, Syuzanna; and Michrowska, Anna; "A Highly Efficient Ruthenium Catalyst for Metathesis Reactions"; Angew. Chem. 2002, vol. 21, No. 21. pp. 4210-4212.

(Continued)

Primary Examiner — Yong Chu
(74) Attorney, Agent, or Firm — RatnerPrestia

(57) ABSTRACT

A self-metathesis process for the production of unsaturated dicarboxylic fatty diacids and/or unsaturated dicarboxylic fatty diesters, wherein unsaturated carboxylic fatty acids and/or esters of unsaturated carboxylic fatty acids are reacted in the presence of at least one defined ruthenium based catalyst compound. A catalyst enhancer compound selected from a sacrificial catalyst or a non-catalyst enhancer may also be used. The process exhibits improved reaction times and/or the catalyst can be used at very low concentrations.

15 Claims, No Drawings

(56) References Cited

FOREIGN PATENT DOCUMENTS

| WO | WO 2008/034552 | 3/2008 |
|----|----|----|
| WO | WO 2008/065187 | 6/2008 |
| WO | WO 2008/065187 A1 | 6/2008 |
| WO | 2009020667 A1 | 2/2009 |
| WO | 2012143067 A1 | 10/2012 |

OTHER PUBLICATIONS

Wakamatsu, Hideaki and Blecher, Siegfried,; "A New Highly Efficient Ruthenium Metathesis Catalyst"; Angew. Chem. 2002, vol. 114, No. 13, pp. 2509-2511.

Wakamatsu, Hideaki and Blecher, Siegfried,; "Ein Hochaktiver und Luftstabiler Rutheniumkomplex für die Olefinmethathese" With English Abstract (English Title: "A Highly Active and Air-Stable Ruthenoum Complex for Olefin Metathesis"); Angew. Chem. 2002, vol. 114, No. 5, pp. 832-834(German Publication) (pp. 794-796 English Publication).

Slugovc, Christian; Perner, Bernahard; Stelzer, Franz and Mereiter, Kurt: ""Second Generation Ruthenium Carbene Complexes With a Cis-Dichloro Arrangement""; Organometallics 2004, vol. 23, pp. 3622-3626.

Nolan, S.P. et al.; "Towards Long-Living Metathesis Catalyst by Tuning the N-Heterocyclic Carbene (NHC) Ligand on Thrifuroacetmide-Activated Boomerang Ru Complexes", European Journal of Orgainic Chemistry, Jul. 6, 2009, Issue 25, pp. 4254-4265.

Kingsbury, Jason S.; Harrity, Joseph P.A.; Bonitatebus, Jr., Peter J.; and Hoveyda, Amir H. "A Recyclable Ru Based Metathese Catalyst"; American Chemical Society 199, vol. 121, pp. 791-799.

International Search Report of WO2013/14044(PCT/GB2013/050684), dated July 10, 2013.

Thomas, P.A. et al., "Metathesis of Fatty Acid Ester Derivatives in 1,1-Dialkyl and 1,2,3-Trialkyl Imidazolium Type Ionic Liquids", Int. J. Mol, Sci.; vol. 12, Jun. 14, 2011 (Jun. 14, 2011), pp. 3989-3997.

Schrodi Yann et al., "Ruthenium Olefin Metathesis Catalysts for the Ethenolysis of Renewable Feedstocks", Clean—Soil, Air, Water, Wiley-VCH Verlag GMGH & Co. KGAA, DE, vol. 36, No. 8, Jan. 1, 2008, pp. 669-673.

Ngo H. L. et al.: Metathesis of Unsaturated Fatty Acids: Synthesis of Long-Chain Unsaturaed-Alpha, Omega-Dicarboxylic Acids:, Journal of the American Oil Chemists Society, USAOCS Press, Champaign, IL, vol. 83, No. 7, Jul. 1, 2006 , pp. 629-634.

Mudassar Abbas et al.: "Optimized Reaction Conditions for the Cross-Metathesis of Methyl Oleate and Oleylamine Wih Ethyl Acrylate"; Monatshefte fur Chemie—Chemical Monthly: and International Journal of Chemistry, Springer-Verlag; vol. 143, No. 4, Jan. 24, 2012; pp. 669-673.

Slugovc C et al."Second Generation Ruthenium Carbene Compleses With a Cis-Dichloro Arrangement", Organometallics, ACS, vol. 23, No. 15, Jul. 19, 2004, pp. 3622-3626.

Bargiggia et al., "Cross-meathesis assisted bty microwave irradiation", The Journal of ORganic Chemistry, American Chemical Society, vol. 70, Jan. 1, 2005, pp. 9636-9639.

European Examination Report for EP Application No. 13712897.1, dated Mar. 14, 2016.

International Search Report for WO2013/14045 (PCT/GB2013/050685), dated Jul. 5, 2013, pp. 1-3.

IW. Meyer et al., "Tin and Iron Halogenides as Additives in Ruthenium-Catalyzed Olefin Metathesis", Inorganica Chimca ACTA, Elsevier VV, NL., vol. 359, No. 9, Jun. 1, 2006, pp. 2910-2917.

Akshai Kumar et al., "Metathesis of Carbon Dioxide and Phenyl Isocyanate Catalysed by Group (IV) Metal Alkoxides: An Experimental and Computational Study", Journal of Chemical Sciences [(Formerly: Proceedings (Chemical Sciences)], Springer-Verlag, India, vol. 123, No. 1, Sep. 9, 2011, pp. 29-36.

Non Final Office Action for U.S. Appl. No. 14/383,348, dated Aug. 11, 2016, 16 pages.

U.S. Notice of Allowance for U.S. Appl. No. 14/383,348, dated Jan. 11, 2017, 15 pages.

Monfette, S., et al., "Equilibrium Ring-Closing Metathesis," Aug. 12, 2009, pp. 3783-3816, vol. 109(8), Chemical Reviews, XP055388545, US, ISSN: 0009-2665, DOI: 10.1021/cr800541y.

European Office Action for European Application No. 13 712 897.1, dated Jul. 13, 2017, 6 pages.

\* cited by examiner

METATHESIS OF OLEFINS USING RUTHENIUM BASED CATALYTIC COMPLEXES

CROSS REFERENCE TO RELATED APPLICATIONS

This application is the U.S. National Phase application of PCT International Application No. PCT/GB2013/050684, filed Mar. 18, 2013, and claims priority of Great Britain Application No. 1204715.5 filed Mar. 18, 2012, the disclosures of which are incorporated herein by reference in their entireties for all purposes.

The present invention relates to a process of self-metathesis of olefin comprising species, and in particular a method of self-metathesising unsaturated carboxylic fatty acids or unsaturated fatty carboxylic esters using ruthenium based catalysts.

Metathesis is a known chemical process in the art. The process typically involves catalytic reactions which result in the interchange of groups on either side of one or more carbon-carbon double bonds in a first molecule with groups on a second unsaturated molecule. Metathesis can therefore be adapted to oleochemical feedstocks.

This group interchange takes place as a result of the formation and cleavage of the carbon-carbon double bonds aided by a catalyst. Several types of metathesis can be defined, including metathesis between two chemically identical molecules (self-metathesis) or between two different compounds (cross-metathesis). A schematic representation of self-metathesis equilibrium process is:

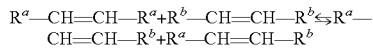
$R^a$—CH=CH—$R^a$+$R^b$—CH=CH—$R^b$⇌$R^a$—CH=CH—$R^b$+$R^a$—CH=CH—$R^b$ where $R^a$ and $R^b$ represent possible organic groups.

Catalysts for this reaction have evolved over the last few years, with a desire for both high efficiency and selectivity. Recently developed homogeneous catalysts are well-defined organometallic compounds which generally fall in to two categories, namely Schrock catalysts and Grubbs' catalysts. Schrock catalysts are based upon molybdenum(VI) and tungsten(VI), whilst Grubbs' catalysts are based upon ruthenium(II) complexes. Generally a second generation of Grubbs' metathesis catalysts have been developed based on carbenoid complexes Ruthenium based metathesis catalysts are known from published patent application WO 02/14376. Further catalysts of this type have also become known and disclosed in Angew. Chem. 2002, 114 No. 5, 832-834, Angew. Chem. 2002, 114, No. 13, 2509-2511, and Angew. Chem. 2002, 114, No. 21, 4210-4212.

These known metathesis catalysts have a number of disadvantages, especially when applied to self-metathesis reactions of oleochemical feedstocks. In particular, the existing catalysts may provide long reaction times (i.e. time for the reaction to reach equilibrium) usually of the order of several hours. This is exemplified in published patent application US 2011/0171147. Longer reaction times can reduce the freedom of the reaction process design, the ability of the reaction operator to further process the reaction product, and the overall efficiency of the process especially where several batch runs or even continuous operation of the process is desired.

Additionally, a further disadvantage of existing self-metathesis catalysts is that they can be liable to loss of catalytic activity over time due to catalyst degradation. The catalysts described in published patent application WO 02/14376 allow for recovery of the catalyst at the end of the reaction, with subsequent re-use. This can be an important factor as the catalysts concerned are typically highly expensive. However, the disclosed catalysts have the disadvantage of exhibiting losses of around 10% per reaction cycle.

The present invention therefore seeks to provide a process of self-metathesis for producing unsaturated dibasic acids and esters, and in particular using unsaturated fatty acids or esters as starting materials, where the process exhibits improved performance, and which reduces or overcomes at least some of the disadvantages of the prior attempts as described herein.

According to a first aspect of the present invention there is provided a self-metathesis process for the production of unsaturated dicarboxylic fatty diacids and/or unsaturated dicarboxylic fatty diesters, wherein unsaturated carboxylic fatty acids and/or esters of unsaturated carboxylic fatty acids are reacted in the presence of at least one catalyst compound of Formula (I) or (II):

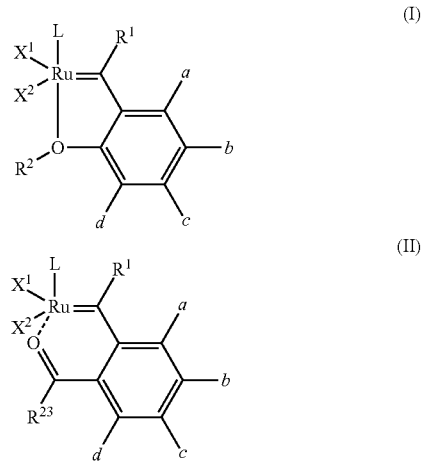

wherein
L represents a neutral, preferably carbene, ligand;
$R^1$ represents hydrogen, $C_1$ to $C_6$ alkyl, $C_2$ to $C_6$ alkenyl, $C_2$ to $C_6$ alkynyl, $C_5$ or $C_6$ aryl, aralkyl, hydroxyl, $C_1$ to $C_6$ alkoxy, aryloxy, or arylalkoxy;
a, b, c, d each independently represent hydrogen, $C_1$ to $C_6$ alkyl, $C_1$ to $C_6$ alkoxy, $C_5$ or $C_6$ aryl, or an electron withdrawing group;
$X^1$ and $X^2$ each independently represent anionic ligands;
$R^2$ represents a $C_1$ to $C_6$ alkyl, $C_5$ or $C_6$ cycloalkyl, $C_5$ or $C_6$ aryl, $C_1$ to $C_6$ alkoxy, aryloxy, arylalkoxy, or alkanone;
$R^{23}$ represents a $C_1$ to $C_6$ alkyl, $C_5$ or $C_6$ cycloalkyl, $C_5$ or $C_6$ aryl, $C_1$ to $C_6$ alkoxy, aryloxy, or arylalkoxy.

According to a second aspect of the present invention there is provided the use of a catalyst enhancer compound to at least double the efficiency of the catalyst compound of Formula (I) or (II) defined herein, in the self-metathesis process defined herein.

According to a third aspect of the present invention there is provided unsaturated dicarboxylic fatty diacids and/or unsaturated dicarboxylic fatty diesters formed by the self-metathesis process defined herein.

It has been found that the use of the catalysts of general Formula (I) or (II) defined herein allow for faster reaction times and/or improved performance of self-metathesis reactions for unsaturated dicarboxylic fatty diacids and/or unsaturated dicarboxylic fatty diesters. Use of these catalysts also allows for lower concentrations of catalysts to be used in the self-metathesis process.

Reduced reaction times have also been found, and this allows for more freedom for processing reaction products. It is also provides for simpler implementation of a continuous or semi-continuous process, often typified by relatively small reaction volumes, as a higher number of reactions can be performed within a given period of time. In the event of a continuous process, this means a relatively high throughput of starting olefin can be achieved in a reactor of moderate volume.

It has also been found that relatively low rates of catalyst degradation are achieved. This may be advantageous for batch processes as the reaction mixture does not have to be subjected to immediate processing to remove the catalyst in order to preserve it. Additionally, this may be advantageous for continuous processes as the catalyst does not significantly degrade over several reaction cycles.

As used herein, the terms 'metathesise' and 'metathesising' refer to the reacting of a feedstock in the presence of a metathesis catalyst to form a metathesis product comprising a new olefinic compound.

The term 'self-metathesis' as used herein, unless otherwise defined, refers to any metathesis reaction in which two carbon-carbon double bonds (i.e. unsaturated), each of which is present on a separate molecule, are reacted together. The two molecules are identical, and therefore the self-metathesis reaction comprises reacting of the carbon-carbon double bonds on the two identical molecules.

Alternatively, self-metathesis also refers to reaction of two carbon-carbon double bonds, each of which is present in identical subunits of a larger molecule. An example would be the reaction between two identical unsaturated fatty acids linked together as part of a single triglyceride molecule. For example, self-metathesis may refer to reacting two of the same triglycerides present in a natural feedstock in the presence of a metathesis catalyst, wherein each triglyceride has an unsaturated carbon-carbon double bond, thereby forming two new olefinic molecules which may include a dimer of the triglyceride.

As used herein, the terms 'for example,' 'for instance,' 'such as,' or 'including' are meant to introduce examples that further clarify more general subject matter. Unless otherwise specified, these examples are provided only as an aid for understanding the applications illustrated in the present disclosure, and are not meant to be limiting in any fashion.

It will be understood that, when describing the number of carbon atoms in a substituent group (e.g. '$C_1$ to $C_6$ alkyl'), the number refers to the total number of carbon atoms present in the substituent group, including any present in any branched groups.

The term 'catalyst' as used herein refers to a compound that facilitates the reaction of interest, in this case self-metathesis, by lowering the rate-limiting free energy of the transition state of the reaction resulting in a larger reaction rate at the same temperature. However, unlike other reagents of the reaction, the catalysts are not consumed by the overall reaction itself. The use of the term 'catalyst' in relation to the process of the present invention shall refer to catalyst compounds of Formula (I) or (II).

Homogeneous metathesis catalysts typically function by dissociation of one or more ligands in solution (the initiating step), which generates the actual productive catalytic species. Strictly speaking the catalyst compounds of Formula (I) or (II) described herein are thus precatalysts. Since the concentration and nature of the actual catalytic species cannot generally be accurately determined, no distinction is commonly made and the two terms can be used interchangeably.

The neutral ligand L may represent a phosphine. Preferably said phosphine has formula —$P(R^3)(R^4)(R^5)$, wherein $R^3$, $R^4$, and $R^5$ each independently represent $C_1$ to $C_6$ alkyl, $C_5$ or $C_6$ cycloalkyl, or aryl.

The term '$C_1$ to $C_6$ alkyl' as used herein, unless otherwise defined, refers to saturated hydrocarbon radicals being straight chain, branched, cyclic, polycyclic moieties, or combinations thereof, containing from 1 to 6 carbon atoms. The $C_1$ to $C_6$ alkyl may be optionally substituted. Examples of suitable substituents may comprise hydroxy, halo, nitro, or amine groups.

Where any of $R^3$, $R^4$, and $R^5$ represent $C_1$ to $C_6$ alkyl, said alkyl may be independently selected from methyl, ethyl, n-propyl, isopropyl, n-butyl, isobutyl, sec-butyl, tert-butyl, 2 methyl-butyl, pentyl, hexyl, cyclohexyl, or the like.

The term 'halo' as used herein, unless otherwise defined, refers to halide radicals derived from elements in Group VII (Group 17) of the periodic table. The halide radicals may be independently selected from fluoro, chloro, bromo, or iodo. Preferably, said halo is selected from fluoro or chloro.

The term 'aryl' as used herein, unless otherwise defined, refers to an organic radical derived from an aromatic hydrocarbon by removal of one hydrogen, and includes any monocyclic, bicyclic, or polycyclic carbon ring of up to 7 members in each ring, wherein at least one of the rings is aromatic. These aryl radicals may optionally be substituted. Examples of suitable substituents comprise hydroxy, $C_1$ to $C_6$ alkoxy, halo, nitro, amines, or $C_1$ to $C_6$ alkyl groups.

Where any of $R^3$, $R^4$, and $R^5$ represent aryl, said aryl may be independently selected from phenyl, p-tolyl, chlorophenyl, nitrophenyl, aminophenyl, methyl-aminophenyl, hydroxyphenyl, methyl-hydroxyphenyl, naphthyl, amino-naphthyl, tetrahydronaphthyl, indanyl, biphenyl, phenanthryl, anthryl, or the like.

Preferably, $R^3$, $R^4$, and $R^5$ each independently represent $C_5$ or $C_6$ cycloalkyl, or aryl. More preferably, $R^3$, $R^4$, and $R^5$ each independently represent $C_5$ or $C_6$ cycloalkyl. Most preferably, the neutral ligand may be —$P(Cy)_3$ in which $R^3$, $R^4$, and $R^5$ each represent cyclohexyl ('Cy').

In an alternative embodiment, the neutral ligand L may be selected from a ligand of any of formulas $L^1$, $L^2$, $L^3$, $L^4$, or $L^5$;

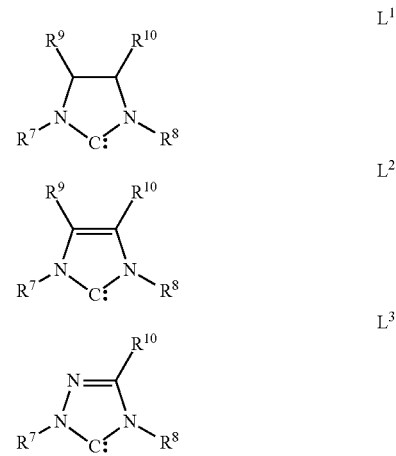

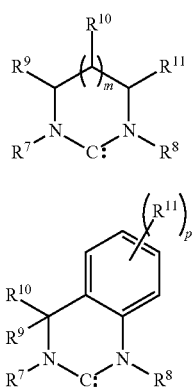

L⁴

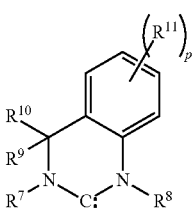

L⁵

$R^9$, $R^{10}$, and $R^{11}$ each independently represent hydrogen, $C_1$ to $C_6$ alkyl, $C_2$ to $C_6$ alkenyl, aryl, or halo. Any adjacent group of $R^9$, $R^{10}$, and $R^{11}$ may form a 3, 4, 5, 6, or 7 membered cycloalkyl, alkylene bridge, or aryl.

Where any of $R^9$, $R^{10}$, and $R^{11}$ represent $C_1$ to $C_6$ alkyl, said alkyl may be independently selected from methyl, ethyl, n-propyl, isopropyl, n-butyl, isobutyl, sec-butyl, tert-butyl, 2 methyl-butyl, pentyl, hexyl, cyclohexyl, or the like.

The term '$C_2$ to $C_6$ alkenyl' as used herein, unless otherwise defined, refers to hydrocarbon radicals having in the range from 1 to 3 carbon-carbon double bonds. The alkenyl radicals may be straight chain, branched, cyclic, polycyclic moieties, or combinations thereof. The alkenyl radicals may each contain from 2 to 6 carbon atoms. The $C_2$ to $C_6$ alkenyl may be optionally substituted. Examples of suitable substituents may comprise hydroxy, halo, nitro, or amine groups.

Where any of $R^9$, $R^{10}$, and $R^{11}$ represent $C_2$ to $C_6$ alkenyl, said alkenyl may be independently selected from vinyl, allyl, isopropenyl, pentenyl, hexenyl, cyclopentenyl, 1-propenyl, 2-butenyl, 2-methyl-2-butenyl, isoprenyl, and the like.

The alkylene bridge may preferably be formed from a $C_2$ to $C_6$ alkenyl, where said alkenyl is as defined herein.

Where any of $R^9$, $R^{10}$, and $R^{11}$ represent aryl, said aryl may be independently selected from phenyl, p-tolyl, chlorophenyl, nitrophenyl, aminophenyl, methyl-aminophenyl, hydroxyphenyl, methyl-hydroxyphenyl, naphthyl, aminonaphthyl, tetrahydronaphthyl, indanyl, biphenyl, phenanthryl, anthryl, or the like.

Preferably, $R^9$, $R^{10}$, and $R^{11}$ each independently represent hydrogen or $C_1$ to $C_6$ alkyl. More preferably, $R^9$, $R^{10}$, and $R^{11}$ each independently represent hydrogen, methyl, ethyl, or butyl. Most preferably, $R^9$, $R^{10}$, and $R^{11}$ each independently represent hydrogen.

For ligand $L^4$, m represents an integer in the range from 1 to 3. For ligand $L^5$, p represents an integer in the range from 0 to 4.

$R^7$ and $R^8$ each independently represent hydrogen, $C_1$ to $C_6$ alkyl, or aryl. More preferably, $R^7$ and $R^8$ each independently represent $C_1$ to $C_6$ alkyl or aryl. Most preferably, $R^7$ and $R^8$ each independently represent aryl.

In a particularly preferred embodiment, $R^7$ and $R^8$ may represent identical groups.

Where $R^7$ and/or $R^8$ represent aryl, said aryl may preferably comprise an aryl substituted by from any of 1 to 5 independently selected groups, more preferably either 2 or 3 groups.

Said substituent groups may preferably be selected from $C_1$ to $C_6$ alkyl, $C_1$ to $C_6$ alkoxy, or halo. More preferably, said substituent groups are $C_1$ to $C_6$ alkyl. Most preferably, said substituent groups are independently selected from methyl, ethyl, n-propyl, isopropyl, n-butyl, isobutyl, sec-butyl, tert-butyl, 2 methyl-butyl, pentyl, hexyl, or cyclohexyl. Particularly preferred substituent groups may be methyl or isopropyl.

In a particularly preferred embodiment, $R^7$ and $R^8$ both represent identical aryl groups comprising 2 or 3 $C_1$ to $C_6$ alkyl substituent groups. More preferably, $R^7$ and $R^8$ are each mesityl (1,3,5-trimethylphenyl) or 2,6-diisopropylphenyl.

Preferably, $R^1$ represents hydrogen or $C_1$ to $C_6$ alkyl. More preferably, $R^1$ represents hydrogen, methyl, ethyl, n-propyl, isopropyl, n-butyl, isobutyl, sec-butyl, tert-butyl, or 2 methyl-butyl. Most preferably, $R^1$ represents hydrogen or methyl. Particularly preferred is where $R^1$ represents hydrogen.

Preferably a, b, c, d each independently represent hydrogen, $C_1$ to $C_6$ alkyl, aryl, or an electron withdrawing group.

Preferably, said $C_1$ to $C_6$ alkyl and aryl may be as previously defined herein with regard to $R^3$.

The term 'electron withdrawing group' (EWG) as used herein has the usual meaning in the art, and refers to a moiety having a relatively high electronegativity and thus a relatively strong tendency to attract electron density from more electron-rich moieties.

Preferably, said EWG may be selected from —$NO_2$, $C_1$ to $C_6$ sulphonamides (—$SO_2NR^{12}R^{13}$), halo, $C_1$ to $C_6$ carbonyl, amine (—$NR^{12}R^{13}R^{14}$), amido (—$C(O)NR^{12}R^{13}$), carbamate (—$OC(O)NR^{15}R^{16}$), or —$NR^{17}C(O)R^{18}$.

Preferably, the EWG is selected from —$NO_2$, sulphonamides (—$SO_2NR^{12}R^{13}$), or —$NR^{17}C(O)R^{18}$. More preferably, the EWG is —$NR^{17}C(O)R^{18}$.

$R^{12}$, $R^{13}$, and $R^{14}$ each independently represent hydrogen, $C_1$ to $C_6$ alkyl, $C_1$ to $C_6$ perhalogenoalkyl, $C_1$ to $C_6$ alkoxy, or halo.

$R^{15}$, $R^{16}$, $R^{17}$, and $R^{18}$ each independently represent hydrogen, $C_1$ to $C_6$ alkyl, $C_1$ to $C_6$ alkoxy, $C_1$ to $C_6$ perhalogenoalkyl, $C_1$ to $C_6$ carbonyl, optionally substituted amide, nitrile, aryl, pyridinium alkyl, pyridinium perhalogenoalkyl, optionally substituted $C_5$ or $C_6$ cyclohexyl, or ester of a $C_1$ to $C_6$ alkyl.

Preferably, $R^{15}$, $R^{16}$, $R^{17}$, and $R^{18}$ each independently represent hydrogen, $C_1$ to $C_6$ alkyl, $C_1$ to $C_6$ alkoxy, $C_1$ to $C_6$ perhalogenoalkyl, $C_1$ to $C_6$ carbonyl, or ester of a $C_1$ to $C_6$ alkyl.

More preferably, $R^{17}$ represents hydrogen or $C_1$ to $C_6$ alkyl. Most preferably, $R^{17}$ represents hydrogen.

More preferably, $R^{15}$, $R^{16}$, and $R^{18}$ each independently represent $C_1$ to $C_6$ alkyl, $C_1$ to $C_6$ alkoxy, $C_1$ to $C_6$ perhalogenoalkyl, $C_1$ to $C_6$ carbonyl, or ester of a $C_1$ to $C_6$ alkyl.

Most preferably, $R^{15}$, $R^{16}$, and $R^{18}$ represent $C_1$ to $C_6$ alkoxy, $C_1$ to $C_6$ perhalogenoalkyl, or ester of a $C_1$ to $C_6$ alkyl.

The term 'perhalogenoalkyl' as used herein, unless otherwise defined, refers to a radical derived from saturated hydrocarbon being straight chain, branched, cyclic, polycyclic moieties, or combinations thereof, containing 1 to 6 carbon atoms, and wherein at least one hydrogen is substituted by fluoro, chloro, bromo, or iodo. Preferably, all hydrogens are substituted by fluoro, chloro, bromo, or iodo. Preferably, all the hydrogens are substituted by fluoro.

Preferably, the perhalogenalkyl group represents trifluoromethyl (—$CF_3$), trichloromethyl (—$CCl_3$), hexafluoroisopropyl (—$CH(CF_3)_2$), heptafluoroisopropyl (—$CF(CF_3)_2$), or heptafluoroethyl (—$CF_2CF_3$). More preferably, the perhalogenalkyl group represents hexafluoroisopropyl (—CH (CF₃)₂), heptafluoroisopropyl (—CF(CF₃)₂), or trifluoromethyl (—CF₃). Most preferably, the perhalogenalkyl group is trifluoromethyl (—CF₃).

The term 'alkoxy' as used herein, unless otherwise defined, refers to alkyl groups linked to oxygen which form an alkoxy radical having the structure —O—$R^{19}$, and which are bonded to an adjacent radical via the oxygen. $R^{19}$ represents a $C_1$ to $C_6$ alkyl group as defined herein.

Examples of alkoxy radicals may be independently selected from methoxy, ethoxy, butoxy, propoxy, amyloxy, cyclohexoxy, or the like. Where $R^{15}$, $R^{16}$, $R^{17}$ and/or $R^{18}$ are a $C_1$ to $C_6$ alkoxy, preferably they each independently represent methoxy, ethoxy, butoxy, or propoxy. More preferably, ethoxy, butoxy, or propoxy. Most preferably, isobutoxy or isopropoxy.

Preferably, the ester of a $C_1$ to $C_6$ alkyl is selected from methyl ester, ethyl ester, propyl ester, butyl ester. More preferably, methyl ester or ethyl ester. Most preferably, ethyl ester.

In an alternative embodiment, any of groups a, b, c, or d may be bonded to either group $R^2$ in general structure (I) or $R^{23}$ in general structure (II). In such an embodiment, any of groups a, b, c, or d may form a cyclic structure with either group $R^2$ in general structure (I) or $R^{23}$ in general structure (II).

In said alternative embodiment, the groups a, b, c, or d which forms the cyclic structure may represent any of the aforementioned substituents as defined herein. In particular, the group which forms the cyclic structure may be an EWG, and most preferably may be —$NR^{17}C(O)R^{18}$.

In this embodiment, $R^{17}$ may preferably be selected from hydrogen, $C_1$ to $C_6$ alkoxy, ester of a $C_1$ to $C_6$ alkyl, and $R^{18}$ may preferably be selected from $C_1$ to $C_6$ alkyl.

The cyclic structure may be formed by any of the atoms in the groups a, b, c, or d bonding to the oxygen to which either $R^2$ or $R^{23}$ would otherwise be bonded. Preferably, substituent d forms the cyclic structure.

Preferably, $R^2$ represents hydrogen, $C_1$ to $C_6$ alkyl, $C_1$ to $C_6$ alkoxy, alkanone, or $C_5$ or $C_6$ cyclohexyl. More preferably, $R^2$ represents $C_1$ to $C_6$ alkyl, $C_1$ to $C_6$ alkoxy, or alkanone. Most preferably, $R^2$ represents $C_1$ to $C_6$ alkyl or an alkanone.

The term 'alkanone' as used herein, unless otherwise defined, refers to a carbonyl comprising group —$(CHR^{20})_nC(O)R^{21}$ where $R^{20}$ and $R^{21}$ are selected from hydrogen, $C_1$ to $C_6$ alkyl, or $C_5$ to $C_6$ cycloalkyl, and where n represents an integer in the range from 1 to 5.

Where $R^2$ is an alkanone, preferably $R^{20}$ and $R^{21}$ each independently represent hydrogen, methyl, or ethyl, and n represents the integer 1. More preferably, $R^{20}$ and $R^{21}$ both represent methyl, and n represents the integer 1.

The term 'aryloxy' as used herein, unless otherwise defined, refers to aryloxy radicals having the structure —O—Ar, and which are bonded to an adjacent radical via the oxygen. Ar represents an aryl group as defined herein.

Examples of aryloxy radicals may be independently selected from phenoxy, naphthyloxy, phenylphenoxy, diphenylphenoxy, triphenylphenoxy, or tetraphenylphenoxy.

The term 'arylalkoxy' as used herein, unless otherwise defined, refers to arylalkoxy radicals having the structure —O—$R^{22}$—Ar, and which are bonded to an adjacent radical via the oxygen. $R^{22}$ represents a $C_1$ to $C_6$ alkyl and Ar represents an aryl group, both as defined herein.

Examples of arylalkoxy radicals may be independently selected from phenylmethoxy, phenylethoxy, naphthlymethoxy, and naphthlyethoxy.

Where $R^2$ is $C_1$ to $C_6$ alkyl, $R^2$ may preferably be selected from methyl, ethyl, n-propyl, isopropyl, n-butyl, isobutyl, sec-butyl, or tert-butyl. More preferably, selected from methyl, ethyl, n-propyl, or isopropyl. Most preferably, $R^2$ is isopropyl.

Preferably, $R^{23}$ represents hydrogen, $C_1$ to $C_6$ alkyl, $C_1$ to $C_6$ alkoxy, alkanone, or $C_5$ or $C_6$ cyclohexyl. More preferably, $R^{23}$ represents $C_1$ to $C_6$ alkyl, or $C_1$ to $C_6$ alkoxy. Most preferably, $R^{23}$ represents $C_1$ to $C_6$ alkoxy.

In particular, $R^{23}$ may be selected from hydrogen, methyl, ethyl, propyl, methoxy, ethoxy, butoxy, propanoxy, amyloxy, cyclohexoxy, or the like. Preferably, $R^{23}$ may be selected from methoxy, ethoxy, or butoxy. Most preferably, $R^{23}$ is methoxy.

In particular, self-metathesis catalysts of general structure (I) are disclosed in WO 2008/065187 and WO 2008/034552, and these documents incorporated herein by reference.

Particularly preferred examples of suitable catalysts having general Formula (I) may be selected from:

[1,3-bis(2,6-diisopropylphenyl)-2-imidazolidinylidene]dichloro[2-(1-methylacetoxy) phenyl]methyleneruthenium (II);

[1,3-bis(2,4,6-trimethylphenyl)-2-imidazolidinylidene]dichloro[2-(1-methylacetoxy) phenyl]methyleneruthenium (II);

[1,3-bis(2,6-diisopropylphenyl)-2-imidazolidinylidene]dichloro[[2-(2-oxopropoxy) phenyl]methylene]ruthenium (II);

[1,3-bis(2,4,6-trimethylphenyl)-2-imidazolidinylidene]dichloro[[2-(2-oxopropoxy) phenyl]methylene]ruthenium (II);

([1,3-bis(2,4,6-trimethylphenyl)-2-imidazolidinyliden]dichloro[(2-isopropoxy)(5-trifluoracetamido)benzyliden]]ruthenium(II));

([1,3-bis(2,6-diisopropylphenyl)-2-imidazolidinyliden]dichloro[(2-isopropoxy)(5-trifluoracetamido)benzyliden]]ruthenium(II));

([1,3-bis(2,6-diisopropylphenyl)-2-imidazolidinyliden]dichloro[(2-isopropoxy)(5-isobutoxyacetamido)benzyliden]]ruthenium(II));

([1,3-bis(2,4,6-trimethylphenyl)-2-imidazolidinyliden]dichloro[(2-isopropoxy)(5-isobutoxyacetamido)benzyliden]]ruthenium(II)); ([1,3-bis(2,6-diisopropylphenyl)-2-imidazolidinyliden]dichloro[(2-isopropoxy)(5-ethylesteracetamido)benzyliden]]ruthenium(II)); or ((1,3-bis(2,6-diisopropylphenyl)-imidazolidin-2-yliden)((2-ethyl-3-oxo-3,4,-dihydro-2H-benzo[b][1,4]oxazin-8-yl)methylene)ruthenium(II)chlorid).

In particular, self-metathesis catalysts of general Formula (II) are disclosed in Organometallics, 2002, 21(2), 331-335 and Organometallics, 2004, 23(15), 3622-3626, and these documents are incorporated herein by reference.

A particularly preferred example of a suitable catalyst of general Formula (II) may be selected from:

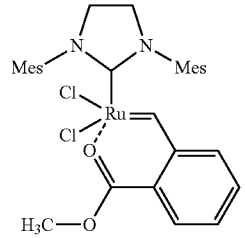

wherein Mes represents mesityl group.

The particularly preferred examples of suitable catalysts that may be used are available commercially from Umicore of Hanau-Wolfgang, Germany.

The starting materials for the self-metathesis process of the present invention comprise unsaturated carboxylic fatty acids and/or esters of unsaturated carboxylic fatty acids. Suitable unsaturated carboxylic fatty acids may be mono- or polyunsaturated carboxylic acids having in the range from 14 to 24 carbon atoms (including the carbonyl carbon atom). Unsaturated carboxylic acids may be represented by the following formula $R^{24}$—COOH, wherein $R^{24}$ represents a mono- or polyunsaturated alkenyl radical having in the range from 14 to 24 carbon atoms (including the carbonyl carbon atom).

The term 'alkenyl' as used herein, unless otherwise defined, refers to hydrocarbon radicals having at least one or a plurality, preferably no more than 6, double bonds. The alkenyl radicals may be straight chain, branched, cyclic, polycyclic moieties, or combinations thereof. The alkenyl radicals may be optionally substituted with a hydroxy, fluoro, chloro, bromo, iodo, nitro, amines, or amides.

$R^{24}$ is preferably acyclic. Preferably, $R^{24}$ is a straight chain alkenyl, and therefore unbranched. Most preferably, $R^{24}$ is an acyclic and straight chain alkenyl.

Particularly preferred as $R^{24}$ are alkenyls having in the range from 1 to 3 carbon-carbon double bonds. Most preferred are mono-unsaturated alkenyl radicals. The carbon-carbon double bond of the fatty chain may be present either in a cis or a trans configuration.

The following nomenclature is used for describing the unsaturated carboxylic acids:
- the first number describes the total number of carbon atoms in the carboxylic acids (including the carbonyl carbon),
- the second number describes the number of carbon-carbon double bonds, and
- the number in brackets describes the position of the double bond relative to the carboxylic acid group.

By way of example, the shorthand for oleic acid is 18:1 (9). If the carbon-carbon double bond is in the trans configuration, this is denoted by the abbreviation 'tr'. Therefore, the shorthand for elaidic acid is 18:1 (tr9).

Suitable monounsaturated carboxylic acids are, for example, myristoleic acids [14:1 (9), (9Z)-tetradeca-9-enoic acid], palmitoleic acid [16:1 (9); (9Z)-hexadeca-9-enoic acid], petroselic acid [(6Z)-octadeca-6-enoic acid], oleic acid [18:1 (9); (9Z)-octadeca-9-enoic acid], elaidic acid [18:1 (tr9); (9E)-octadeca-9-enoic acid)], vaccenic acid [18:1 (tr11); (11E)-octadeca-11-enoic acid], gadoleic acid [20:1 (9); (9Z)-eicosa-9-enoic acid], eicosenoic acid (=gondoic acid) [20:1 (11); (11Z)-eicosa-11-enoic acid], cetoleic acids [22:1 (11); (11Z)-docosa-11-enoic acid], erucic acid [22:1 (13); (13Z)-docosa-13-enoic acid], brassidic acid [22:1 (tr13); (13E)-docosa-13-enoic acid], nervonic acid [24:1 (15); (15Z)-tetracosa-15-enoic acid].

Suitable polyunsaturated carboxylic acids are, for example, linoleic acid [18:2 (9,12); (9Z-12Z)-octadeca-9, 12-dienoic acid], alpha-linolenic acid [18:3 (9,12,15); (9Z, 12Z,15Z)-octadeca-9,12,15-trienoic acid], gamma-linolenic acid [18:3 (6,9,12); (6Z,9Z,12Z)-octadeca-6,9,12-trienoic acid], calendic acid [18:3 (8,10,12); (8E,10E,12Z)-octadeca-8,10,12-trienoic acid], punicic acid [18:3 (9,11,13); (9Z,11E, 13Z)-octadeca-9,11,13-trienoic acid], alpha-eleostearic acid [18:3 (9,11,13); (9Z,11E,13E)-octadeca-9,11,13-trienoic acid], arachidonic acid [20:4 (5,8,11,14), (5Z,8Z,11Z,14Z)-eicosa-5,8,11,14-tetraenoic acid], timnodonic acid [20:5 (5,8,11,14,17), (5Z,8Z,11Z,14Z,17Z)-eicosa-5,8,11,14,17-pentaenoic acid], clupandodonic acid [22:5 (7,10,13,16,19), (7Z,10Z,13Z,16Z,19Z)-docosa-7,10,13,16,19-pentaenoic acid], cervonic acid [22:6 (4,7,10,13,16,19), (4Z,7Z,10Z, 13Z,16Z,19Z)-docosa-4,7,10,13,16,19-hexaenoic acid].

Monounsaturated carboxylic acids are preferred. In particular, monounsaturated carboxylic acids selected from oleic acid [18:1 (9); (9Z)-octadeca-9-enoic acid], elaidic acid [18:1 (tr9); (9E)-octadeca-9-enoic acid], erucic acid [22:1 (13); (13Z)-docosa-13-enoic acid], and brassidic acid [22:1 (tr13); (13E)-docosa-13-enoic acid] are preferred.

The esters of unsaturated carboxylic fatty acids for use in the self-metathesis process of the present invention comprise esters of the unsaturated carboxylic acids as defined herein. In particular esters are those formed from unsaturated carboxylic acids, as defined herein, with alcohols represented by the following formula $R^{25}$—OH.

$R^{25}$ represents $C_1$ to $C_{14}$ alkyl, $C_1$ to $C_{14}$ alkenyl, or $C_1$ to $C_{14}$ aryl radical.

The $C_1$ to $C_{14}$ alkyl, $C_1$ to $C_{14}$ alkenyl, or $C_1$ to $C_{14}$ aryl radicals may optionally comprise one or more substituents, said substituents selected from hydroxy, $C_2$ to $C_6$ alkenyl, $C_1$ to $C_6$ alkyl, $C_1$ to $C_6$ alkoxy, fluoro, chloro, bromo, iodo, nitro, or aryl.

$R^{25}$ may, by way of example, represent methyl, ethyl, n-propyl, isopropyl, n-butyl, isobutyl, sec-butyl, tert-butyl, 2-methylpropyl, pentyl, 2,2-dimethylpropyl, 2-methylbutyl, 3-methylbutyl, hexyl, 1-methylpentyl, 2-methylpentyl, 3-methylpenyl, 4-methylpentyl, 1-ethylbutyl, 2-ethylbutyl, heptyl, octyl, phenyl, methoxyphenyl, dimethoxyphenyl, chlorophenyl, nitrophenyl, ethenyl, propenyl, or butenyl radicals.

$R^{25}$ may preferably represent methyl, ethyl, n-propyl, isopropyl, n-butyl, isobutyl, sec-butyl, or tert-butyl.

Particularly preferred ester starting materials may be methyl oleate, ethyl oleate, or isopropyl oleate.

Suitable ester starting materials may also include esters of the mono- or polyunsaturated carboxylic acids, as defined herein, with glycerol (glycerol esters). Glycerol esters may be selected from glycerol monoesters (monoglycerides, monoacylglycerol), glycerol diesters (diglycerides, diacyl glycerol), and also glycerol triesters (triglycerides, triacylglyceryl), or combinations thereof.

The unsaturated carboxylic acids or the esters of the unsaturated carboxylic acids as used for the self-metathesis process, may be homogeneous in that the starting material is comprised of only one specific acid or ester selected from the above listed groups.

In the alternative, the starting material may be heterogeneous in that it comprises a mixture, either as a mixture of a number of different acids or a number of different esters, or as a mixture of acids and esters.

In practice the starting materials are most often derived from natural oils, and as such usually the fatty acid component of the starting material (either in the form of a free acid or as the various esters) will consist of multiple similar constituents depending on the source of the fatty acid.

Where heterogeneous mixtures are used, it is preferred that the fatty acid components are at least 60 wt. % of a single identity. More preferably, at least 80 wt. % of a single identity. Most preferably, at least 90 wt. % of a single identity.

The self-metathesis process according to the invention may be carried out at temperatures in the range of from 0° C. to 140° C., preferably in the range of from 25° C. to 120° C., more preferably in the range of from 60° C. to 100° C.

The temperature of the self-metathesis process may represent an important factor in maximising conversion, with each catalyst and starting material having a preferred optimum temperature.

The process may be undertaken in customary solvents in which the starting materials and the catalyst dissolve. Examples of suitable solvents may be those based upon hydrocarbons or alcohols.

In a preferred embodiment of the invention, the method can be carried out without a solvent.

The self-metathesis process is an equilibrium reaction wherein the position of the equilibrium between unreacted unsaturated carboxylic acids and/or esters of the feedstock, and reacted dicarboxylic acids and diesters may vary depending on a number of factors including feedstock properties, catalyst used, and other process conditions. It is noted that different natural oil feedstocks may have different maximum theoretical conversion limits.

The level of conversion for the self-metathesis process of the present invention is therefore defined as the weight percentage of the acid or ester in the starting material which has been consumed by the reaction process and reacted to form the respective diacid or diester at the point when the process has reached equilibrium. For the purposes of defining a level of conversion and equilibrium a closed batch process system should be considered.

Preferably, the level of conversion of the present process is at least 30 wt. %. More preferably, the level of conversion of the process is at least 35 wt. %. Even more preferably, the level of conversion of the process is at least 40 wt. %. Further preferably, the level of conversion of the process is at least 45 wt. %. More preferably, the level of conversion of the process is at least 50 wt. %. Particularly preferred is a conversion level of at least 55 wt. %. A conversion level for the process of at least 60 wt. % may be preferred under optimal conditions.

The time to reach equilibrium is preferably less than 1 hour, more preferably less than 30 minutes, even more preferably less than 20 minutes, further preferably less than 10 minutes, particularly preferably less than 5 minutes, particularly advantageously less than 2 minutes, and most preferably less than 1 minute.

The time to reach equilibrium may be more than 0.5 seconds, more than 1 second, and more than 5 seconds.

It has been found that use of the catalysts as defined in the present invention allow for reaching equilibrium and levels of conversion at particularly low reaction times when using low concentrations of catalyst.

The concentration of catalyst required in order to achieve equilibrium for the self-metathesis process is preferably less than 200 ppm, more preferably less than 100 ppm, more preferably 50 ppm, more preferably less than 30 ppm, even more preferably less than 20 ppm, further preferably less than 10 ppm, particularly preferably less than 5 ppm, and most preferably less than 4 ppm.

The concentration of catalyst required in order to achieve the level of conversion for the self-metathesis process may be more than 0.01 ppm, preferably more than 1 ppm, more preferably more than 2 ppm, even more preferably more than 3 ppm.

A particularly preferred concentration of catalyst required to achieve the level of conversion, and therefore the time to reach equilibrium, is between 3 and 5 ppm.

It has therefore been found that use of the catalysts defined in the present invention allow for reaching equilibrium and levels of conversion at particularly low reaction times when using low concentrations of catalyst.

The level of conversion and reaction times of the self-metathesis process may be determined by the GC-analysis of the reaction products, as described herein.

The 'catalyst efficiency' is defined as the time taken for the reaction process to reach equilibrium (in minutes) as a function of the amount of catalyst present (i.e. per ppm of catalyst). Therefore, a value for catalyst efficiency for any specific reaction can be calculated by multiplying time taken for the reaction process to reach equilibrium (in minutes) by the concentration of catalyst used (in ppm). For example, if equilibrium is reached in 1 minute with a concentration of 3 ppm of catalyst, the catalyst efficiency value will be 3.

The catalyst efficiency for the self-metathesis process according to the present invention is preferably less than 500, more preferably less than 200, even more preferably less than 100, further preferably less than 70, particularly preferably less than 50, more preferably less than 30, even more preferably less than 20, further preferably less than 10, most preferably less than 3.

When referring to catalysts, a known term of art is turnover frequency. This provides an indication of the number of reactions per unit of time (per second typically). This would relate to the value of time taken for the reaction process to reach equilibrium (in minutes) which is used in calculating catalyst efficiency as described above. The turnover frequency may therefore be defined as the turnover number divided by reaction time in seconds. Since self-metathesis reactions are fully reversible and yield a statistical product mixture, it is not possible to accurately measure non-productive events where the product is identical to the starting material. Similarly, metathesis events are typically driven by a ligand-dissociated species, and the concentration of which cannot be accurately determined. Therefore we refer to effective turnover frequency, i.e. the number of starting material molecules converted to products per molecule of the catalyst precursor.

The effective initial turnover frequency of the catalyst for the self-metathesis process according to the invention is suitably in the range from 10 to 50,000. Preferably, the turnover frequency is in the range from 5,000 to 20,000. More preferably, the turnover frequency is in the range from 5,000 to 15,000.

One advantage of the present invention is that due to the catalyst stability and reduced levels of degradation, the catalyst may be able to catalyse a number of reactions without being subjected to regeneration. This may be particularly advantageous when performing the metathesis reaction in a continuous system where multiple reaction cycles are done.

When referring to catalysts, a known term of art is effective turnover number. This provides an indication of the number of molecules of starting material, e.g. methyl oleate converted to products per molecule of the catalyst precursor. Effective turnover numbers are calculated by dividing the number of moles of starting material converted by the number of moles of catalyst.

The turnover number of the catalyst for the self-metathesis process according to the invention is suitably in the range from 5,000 to 1,000,000. Preferably, the turnover number is in the range from 20,000 to 500,000. More preferably, the turnover number is in the range from 200,000 to 350,000.

Catalyst stability may be defined as the time the catalyst remains stable and able to undertake the catalysis of the self-metathesis reaction. Catalysts would be considered no longer stable once they are unable to be recycled or re-used. The catalyst stability for the self-metathesis process according to the invention is suitably greater than 5 minutes. Preferably, greater than 15 minutes. More preferably, greater than 60 minutes of use.

Catalyst activity is defined as the ability of the catalyst to continue catalysing the reaction at a certain speed. Catalyst activity values are expressed as the percentage retention of activity. For example, 100% retention of activity means that the same degree of conversion occurs on a second or subsequent reaction cycle as occurred on the first reaction cycle.

On first use, the catalyst may for example be able to catalyse the metathesis reaction to over 90% of the equilibrium level of conversion within 2 minutes under certain reaction conditions. The catalyst activity is deemed unchanged if it is able to catalyse a freshly added amount of starting material to within the same theoretical conversion in the same time.

Preferably, the catalyst for the self-metathesis process according to the invention is sufficiently stable to retain over 50% of its activity after 30 minutes use. More preferably, the catalyst will be able to retain over 75% of its activity after 30 minutes. Most preferably, the catalyst will be able to retain over 85% of its activity after 30 minutes. The catalyst activity is suitably measured under continuous reaction conditions.

As used herein, the term 'catalyst poison' includes any chemical species or impurity in a feedstock that reduces or is capable of reducing the functionality (e.g. efficiency, conversion, turnover number) of the metathesis catalyst compounds of Formula (I) or (II).

The catalyst poisons may be peroxides, including any and all peroxides, such as hydrogen peroxides, or may be non-peroxide poisons or other catalyst poisons which may include catalyst poisons other than peroxides that may be found in, for example, natural oil feedstocks. These non-peroxide poisons include, but are not limited to, water, aldehydes, alcohols, by-products from oxidative degradation, terminal conjugated polyenes, free fatty acids, free glycerin, aliphatic alcohols, nitriles, esters with unsaturated groups adjacent to ester groups, d-sphingosine, amines, sulphur containing compounds, phosphorous containing compounds, and additional impurities.

It is known in the art for a metathesis starting material to be purified by passing over an amount of aluminium oxide between 25 wt. % and 50 wt. %. It is generally assumed that this treatment effectively removes all catalyst poisons from the starting material. It will be also generally recognised that such a procedure is difficult and/or expensive to implement at large scale in a manufacturing plant environment. The present invention therefore provides a method of overcoming this problem.

Preferably, the process of the invention does not include any chemical treatment of the feedstock or starting material in order to remove catalyst poisons.

An antioxidant may be added to the starting material, preferably in the range from 0.1 ppm to 50 ppm, more preferably in the range from 0.5 ppm to 20 ppm, most preferably in the range from 1 ppm to 10 ppm.

Suitable antioxidants may be selected from t-butylhydroquinone (TBHQ) or butylated hydroxytoluene (BHT), dihydroxytoluene, stearic hydrazide, or 2,6-di-tert-butyl-4-methylphenol. Preferably, the antioxidant may be TBHQ.

Said antioxidants have been found to enhance the oxidative stability, reduce or prevent formation of poisons, and increase shelf life of the starting material prior to use in the self-metathesis process.

The antioxidant may be added to the starting material when the starting material is manufactured. By this method, the level of catalyst poisons formed in the starting material may be kept at a relatively low level, such that there is no need to remove catalyst poisons before performing the metathesis reaction. In particular, the formation of peroxide in the starting material may be at least partially inhibited due to the presence of an antioxidant.

The addition of an antioxidant therefore prevents formation of catalyst poisons, and may therefore be an advantageous step when compared to allowing the poisons to form and subsequently treating the starting material before use to cause their removal.

Preferably, the starting material for the self-metathesis process according to the present invention may comprise a level of peroxide of less than 5 meq/kg. More preferably, the level of peroxide may be less than 3 meq/kg. More preferably, the level of peroxide may be less than 2 meq/kg. Most preferably, the level of peroxide may be less than 1 meq/kg.

The water content of the starting material for the self-metathesis process may be less than 0.1 wt %. Preferably, the water content is less than 0.05 wt %. More preferably, the water content is less than 0.04 wt %. Most preferably, the water content is less than 0.03 wt %.

The hydroxyl value of the starting material for the self-metathesis process may be less than 0.1 mg(KOH)·g$^{-1}$. Preferably, the hydroxyl value is less than 0.05 mg(KOH)·g$^{-1}$. More preferably, the hydroxyl value is less than 0.04 mg(KOH)·g$^{-1}$. Most preferably, the hydroxyl value is less than 0.03 mg(KOH)·g$^{-1}$.

Hydroxyl Values (OH) were measured using a method based upon BS 684 Section 2.9 (1976) and results are quoted in mg(KOH)·g$^{-1}$ (sample) and are corrected for the contribution of acid OH groups.

The acid value of the starting material for the self-metathesis process may be less than 0.20 mg(KOH)·g$^{-1}$. Preferably, the acid value is less than 0.10 mg(KOH)·g$^{-1}$. More preferably, the acid value is less than 0.05 mg(KOH)·g$^{-1}$.

The acid value was measured using the A.O.C.S. Official method Te 1a-64 (Reapproved 1997), and expressed as the number of milligrams of potassium hydroxide required to neutralise the free fatty acids in one gram of sample.

Preferably, the water content, hydroxyl value, and acid value of the starting material are all within the ranges defined herein. Values which are above the ranges defined herein may result in reduced reaction performance and/or catalyst poisoning.

The self-metathesis process according to the present invention may additionally comprise the presence of a catalyst enhancer compound. Said catalyst enhancer compound may be any compound which reacts with catalyst poisons in preference to the reaction of the poisons with the catalyst compounds of Formula (I) or (II) defined herein and used in the process according to the present invention. The catalyst enhancer compounds preferably do not take part, and are not consumed, in the self-metathesis reaction.

The catalyst enhancer may be selected from a sacrificial catalyst, or alternatively may be a selected from a non-catalyst enhancer. The catalyst enhancer compound is preferably a non-catalyst enhancer.

As used herein, the term 'sacrificial catalyst' includes any chemical which could otherwise act as a metathesis catalyst, but which when used in the process of the present invention reacts with catalyst poisons, suitably in preference to reaction of the poisons with the self-metathesis catalyst compound of Formula (I) or (II). By definition, the sacrificial catalyst excludes catalyst compounds of Formula (I) or (II).

The sacrificial catalyst may be selected from, but not limited to, any metathesis catalyst. In particular, the sacrificial catalyst may be selected from organometallic compounds, and preferably metathesis catalysts based on ruthenium, molybdenum, tungsten, rhenium, or titanium. These can be heterogeneous or homogeneous metathesis catalysts. In particular, metathesis catalysts selected from transition metal carbene complexes which may act as catalysts for olefin metathesis are preferred.

The sacrificial catalyst may be selected from catalysts disclosed in US2011/0171147, WO 07/010,453, WO 03/062253, WO 00/015339 and these documents are incorporated herein by reference.

The sacrificial catalyst may, in particular, be selected from dichloro-(3-phenyl-1H-inden-1-ylidene)bis(tricyclohexylphosphine)ruthenium(II), dichloro-(3-phenyl-1H-inden-1-ylidene)bis(isobutylphobane)ruthenium(II), [1,3-bis(2,4,6-trimethylphenyl)-2-imidazolidinylidene]dichloro-(3-phenyl-1H-inden-1-ylidene)(tricyclohexylphosphine)ruthenium(II), [1,3-bis(2,4,6-trimethylphenyl)-2-imidazolidinylidene]dichloro-(3-phenyl-1H-inden-1-ylidene)(pyridyl)ruthenium(II), [1,3-Bis(2,4,6-trimethylphenyl)-2-imidazolidinylidene]-[2-[[(4-methylphenyl)imino]methyl]-4-nitro-phenolyl]chloro-[3-phenyl-indenylidene]ruthenium(II), and [1,3-Bis(2,4,6-trimethylphenyl)-2-imidazolidinylidene]-[2-[[(2-methylphenyl)imino]methyl]-phenolyl]chloro-(3-phenyl-indenylidene)ruthenium(II).

Most preferably, the sacrificial catalyst may be selected from dichloro-(3-phenyl-1H-inden-1-ylidene)bis(tricyclohexylphosphine)ruthenium(II), dichloro-(3-phenyl-1H-inden-1-ylidene)bis(isobutylphobane)ruthenium(II), or [1,3-bis(2,4,6-trimethylphenyl)-2-imidazolidinylidene]dichloro-(3-phenyl-1H-inden-1-ylidene)(tricyclohexylphosphine)ruthenium(II).

The sacrificial catalyst may be added during the reaction process, prior to the start of the process, or alternatively at the same time as the metathesis catalyst is added. In a preferred embodiment, the sacrificial catalyst compound is added substantially simultaneously with the metathesis catalyst at the start of the reaction.

Preferably, an amount of between 1 ppm and 100 ppm of the sacrificial catalyst is added to the reaction mixture, more preferably an amount between 5 ppm and 50 ppm is added, and most preferably 10 ppm and 30 ppm is added.

The sacrificial catalyst may be added to the reaction mixture such that the ratio of the number of moles of the sacrificial catalyst to number of moles of poison is in the range from 0.4 to 2.5:1. Preferably, in the range from 0.6 to 2.0:1. More preferably, in the range from 0.8 to 1.5:1.

As used herein, the term 'non-catalyst enhancer' includes any chemical which when added to the process of the present invention reacts with catalyst poisons, suitably in preference to reaction of the poisons with the self-metathesis catalyst compounds of Formula (I) or (II). The term excludes chemicals which would otherwise act as metathesis catalysts, and therefore does not include those compounds defined as sacrificial catalysts herein.

The non-catalyst enhancer may be selected from a Lewis acid. The non-catalyst enhancer compound may be selected from, but not limited to, Lewis acids. Alternatively, the non-catalyst enhancer compound may be selected from, but not limited to, organometallic compounds with either free coordination (ligand bonding) sites or the ability to dissociate ligand(s) and thus create free coordination sites. Said dissociable ligand may be bonded to the metal ion via an oxygen atom.

The non-catalyst enhancer compound may be selected from copper iodide, sodium iodide, tetrabutylgermanium, tetraethylsilicon, tin oxide, tin octoate, tin oxalate, dibutyltin dilaurate, tin(IV) chloridetetrabutyl orthotitanate, palladium acetate, tris(dibenzylideneacetone)palladium, tetrakis(triphenylphosphine)palladium, bis(diphenylferrocenyl)palladium dichloride, aluminium isopropoxide, aluminium chloride, aluminium bromide, nickel chloride, bis(cyclooctadiene)nickel, nickelocene iron chloride, iron bromide, ferrocene, silver chloride, silver iodide, silver oxide, iodine, silver trifluoromethanesulfonate, boron trifluoride, boron trichloride, boron triiodide, boron tribromide, sodium borohydride and derivates thereof, boric acid, zinc ethylhexanoate, zircon (IV) oxide chloride octahydrate, acetic acid, butylated hydroxytoluene (BHT), quinones, activated charcoal, alumina, and bleaching earth.

Preferred Lewis acids may be selected from boron trifluoride, boron trichloride, boron triiodide, boron tribromide, and derivates thereof. Most preferably, said Lewis acid is boron trifluoride.

The non-catalyst enhancer compound may be selected from titanium based compounds. In particular, non-catalyst enhancer compound may be selected from titanium compounds having the general formula Ti.[Q]$_4$ wherein each Q independently represents hydrogen, a $C_1$ to $C_{10}$ alkoxy group, a halide, a $C_4$ to $C_8$ aryl group, a $C_{12}$ to $C_{18}$ fatty alcohol or a $C_6$ to $C_{18}$ fatty acid.

Said $C_1$ to $C_{10}$ alkoxy group refers to alkyl groups linked to oxygen which form an alkoxy radical, and which are bonded to the titanium atom via the oxygen. The term '$C_1$ to $C_{10}$ alkyl' as used herein, unless otherwise defined, refers to saturated hydrocarbon radicals being straight chain, branched, cyclic, or combinations thereof, containing from 1 to 10 carbon atoms. The $C_1$ to $C_{10}$ alkyl may be optionally substituted for example by hydroxyl groups, and may optionally consist of more than one covalently linked alkoxy radical.

Said $C_1$ to $C_{10}$ alkyl may be independently selected from methyl, ethyl, n-propyl, isopropyl, n-butyl, isobutyl, sec-butyl, tert-butyl, 2 methyl-ethyl, 2 methyl-propyl, 2 methyl-butyl, 2 methyl-pentyl, 2 methyl hexyl, 2 methyl-heptanyl, 2 methyl-octyl, 2 ethyl-propyl, 2 ethyl-butyl, 2 ethyl-pentyl, 2 ethyl-hexyl, 2 ethyl-heptanyl, 2-ethyl-1,3-hexanediol, pentyl, hexyl, cyclohexyl, or the like. Preferably, said $C_1$ to $C_{10}$ alkyl is selected from methyl, ethyl, n-propyl, isopropyl, n-butyl, isobutyl, sec-butyl, tert-butyl, 2 methyl-pentyl, 2 methyl hexyl, 2 ethyl-pentyl, or 2 ethyl-hexyl. Most preferably, said $C_1$ to $C_{10}$ alkyl is selected from ethyl or 2 ethyl-hexyl.

The term 'halide' as used herein, halide radicals derived from elements in Group VII (Group 17) of the periodic table. The halide radicals may be independently selected from fluoro, chloro, bromo, or iodo.

The term '$C_4$ to $C_8$ aryl' refers to an organic radical derived from an aromatic hydrocarbon by removal of one hydrogen, and includes any monocyclic carbon ring of between 4 and 7 members. The $C_4$ to $C_8$ aryl may optionally be substituted. Said $C_4$ to $C_8$ aryl may be independently selected from cyclobutadienyl, cyclopentadienyl, cyclohexadienyl, cycloheptadienyl, cyclooctadienyl, or benzyl. Preferably, said $C_4$ to $C_8$ aryl' is independently selected from cyclopentadienyl or cyclohexadienyl. A specifically preferred titanium based compound comprising a $C_4$ to $C_8$ aryl may be bis(cyclopentadienyl)titanium(IV)dichloride.

The $C_6$ to $C_{18}$ fatty acid, may be selected from linear or branched unsaturated fatty acids. The unsaturated fatty acids may be selected from fatty acids having either a cis/trans configuration, and may have one or more than one unsaturated double bonds. Preferably, the fatty acids used are linear monounsaturated fatty acids.

Suitable $C_6$ to $C_{18}$ fatty acids are preferably selected from caproic acid, caprylic acid, capric acid, lauric acid, myristic acid, or palmitic acid. More preferably, caprylic acid or lauric acid.

The titanium based compounds may comprise bidentate Q ligands, e.g. covalently linked multiple alkoxy radicals. Examples include titanium (IV) oxyacetylacetonate and titanium diisopropoxidebis(2,2,6,6-tetramethyl-3,5-heptanedionate).

Specifically preferred titanium based compounds having general formula Ti.$[Q]_4$ may be selected from titanium (IV) methoxide, titanium (IV) ethoxide, titanium (IV) propoxide, titanium (IV) isopropoxide, titanium (IV) butoxide, titanium (IV) tert-butoxide, titanium (IV) 2-ethylhexoxide, titanium (IV) 2-ethyl-1,3-hexanediolate, titanium (IV) tetrachloride, titanium (IV) tetrabromide, titanium (IV) tetrafluoride, and titanium (IV) tetraiodide.

Preferably, the titanium based compounds are selected from titanium (IV) isopropoxide, titanium (IV) ethoxide, titanium (IV) 2-ethylhexoxide.

The non-catalyst enhancer compound may be added during the reaction process, prior to the start of the process, or alternatively at the same time the catalyst is added. In a preferred embodiment, the non-catalyst enhancer compound is added substantially simultaneously with the metathesis catalyst at the start of the reaction.

Preferably, an amount of between 10 ppm and 1,000 ppm of the non-catalyst enhancer compound is added to the reaction mixture, more preferably an amount between 50 ppm and 300 ppm is added, and most preferably 150 ppm and 250 ppm is added.

The non-catalyst enhancer may be added to the reaction mixture such that the ratio of the number of moles of the non-catalyst enhancer to number of moles of poison is in the range from 2.5 to 10:1. Preferably, in the range from 3 to 8:1. More preferably, in the range from 3.5 to 7:1. Most preferably, in the range from 4 to 6:1.

The catalyst enhancer compound provides for lower levels of catalyst deactivation which therefore allows for lower concentrations of catalyst of Formula (I) or (II) to be used to achieve the same conversion over time, thereby achieving improved levels of catalyst efficiency.

Therefore, with addition of a catalyst enhancer compound, the level of catalyst used in the self-metathesis process according to the invention may preferably be less than 10 ppm, more preferably less than 5 ppm, and most preferably less than 4 ppm.

By use of a catalyst enhancer compound the amount of catalyst of Formula (I) or (II) can be reduced to half of the otherwise required loading for a certain conversion. More preferably a third, and most preferable a quarter or less of the catalyst is needed. In other words, the effective efficiency of the catalyst can be at least doubled, at least tripled, or most preferably at least quadrupled by inclusion of a catalyst enhancer compound.

The catalyst efficiency, as defined herein, can be significantly improved in the presence of the catalyst enhancer compound such that the catalyst efficiency value of the catalyst of Formula (I) or (II) is suitably reduced by at least 10%, preferably by an amount in the range from 20% to 99%, more preferably 50% to 90%, particularly 75% to 90%, and especially 80% to 90% compared to the same reaction in the absence of the catalyst enhancer compound.

Advantageously, the catalyst enhancer compound may be combined with antioxidant treatment of the starting material. Said combination may result in the ability to use low amounts of catalyst in the self-metathesis reaction with little or no increase in reaction time.

The self-metathesis process in accordance with the present invention produces unsaturated dicarboxylic acids and unsaturated dicarboxylic diesters, and also the corresponding unsaturated hydrocarbons. The mixture can be separated, for example by distillation, fractional crystallisation, or extraction.

If desired, the products obtained in this way can be subjected to hydrogenation.

The reaction products are not limited in the uses to which they can be applied. By way of example, some uses of the reaction products might include use in sunscreen formulations, polymer building block, personal care formulations, lubricant formulations, as surfactants, or in waxes.

All of the features described herein may be combined with any of the above aspects, in any combination.

In order that the present invention may be more readily understood, reference will now be made, by way of example, to the following description.

It will be understood that all tests and physical properties listed have been determined at atmospheric pressure and room temperature (i.e. 20° C.), unless otherwise stated herein, or unless otherwise stated in the referenced test methods and procedures.

All reactions mentioned in the examples were performed under a nitrogen atmosphere. Before addition of the catalyst, nitrogen gas was bubbled through the reaction mixture while it was being heated to the reaction temperature, and at least for 15 minutes. Selected examples were performed where the reaction feedstock was purified by passing over 25 wt. % of $Al_2O_3$ directly before performing the reaction to remove catalyst poisons.

Reaction conversion was measured by GC analysis. To ensure no further reaction took place between sampling the reaction mixture and measurement of GC, samples were quenched by addition of ethyl vinyl ether.

Full conversion was measured by performing a single reaction with a very high loading of catalyst, which was known to drive the reaction to complete equilibrium. This mixture was thereafter used as a reference to determine relative GC peak heights at full conversion.

EXAMPLE 1

100 g methyl oleate (purified by aluminium-oxide treatment) was heated to 100° C. 13 ppm of ([1,3-bis(2,4,6-trimethylphenyl)-2-imidazolidinyliden]dichloro[(2-isopropoxy)(5-trifluoracetamido)benzyliden]ruthenium(II)) was dissolved in 1 ml toluene, and this was added to the methyl oleate.

After 30 seconds 43.6% conversion was reached, and after 120 seconds the reaction equilibrium conversion was reached. The reaction mixture contained 24.8% 9-octadecene and 25.4% 9-octadecenedioic acid dimethyl ester. A catalyst efficiency value of 26 was achieved.

EXAMPLE 2

100 g methyl oleate (purified by aluminium-oxide treatment) was heated to 100° C. 37 ppm of ([1,3-bis(2,6-diisopropylphenyl)-2-imidazolidinylidene]dichloro[2-(1- methylacetoxy)phenyl]methyleneruthenium(II))  was dissolved in 1 ml toluene, and this was added to the methyl oleate.

After 30 seconds the reaction equilibrium conversion was reached. The reaction mixture contained 25.3% 9-octadecene and 25.2% 9-octadecenedioic acid dimethyl ester. A catalyst efficiency value of 18.5 was achieved.

EXAMPLE 3

100 g methyl oleate (purified by aluminium-oxide treatment) was heated to 100° C. 63 ppm of ((1,3-bis(2,6-diisopropylphenyl)-imidazolidin-2-yliden)((2-ethyl-3-oxo-3,4,-dihydro-2H-benzo[b][1,4]oxazin-8-1)methylene)ruthenium(II)chlorid was dissolved in 1 ml toluene, and this was added to the methyl oleate.

After 30 seconds the reaction equilibrium conversion was reached. The reaction mixture contained 25.1% 9-octadecene and 25.5% 9-octadecenedioic acid dimethyl ester. A catalyst efficiency value of 31.5 was achieved.

EXAMPLE 4

100 g methyl erucate (purified by aluminium-oxide treatment) was heated to 100° C. 105 ppm of ([1,3-bis(2,4,6-trimethylphenyl)-2-imidazolidinyliden]dichloro[(2-isopropoxy)(5-trifluoracetamido)benzyliden]]ruthenium(II) was dissolved in 1 ml toluene, and this was added to the methyl erucate.

After 30 seconds the reaction equilibrium conversion was reached. The reaction mixture contained 20.6% 9-octadecene and 28.4% 13-hexacosanedioic acid dimethyl ester. A catalyst efficiency value of 52.5 was achieved.

EXAMPLE 5

100 g isopropyl oleate (purified by aluminium-oxide treatment) was heated to 100° C. 50 ppm of ([1,3-bis(2,4,6-trimethylphenyl)-2-imidazolidinyliden]dichloro[(2-isopropoxy)(5-trifluoracetamido)benzyliden]]ruthenium(II) was dissolved in 1 ml toluene, and this was added to the isopropyl oleate.

After 30 seconds equilibrium conversion was reached. The reaction mixture contained 51.0% isopropyl oleate, 19.3% 9-octadecene and 23.0% 9-octadecenedioic acid di-isopropyl ester. A catalyst efficiency value of 25 was achieved.

EXAMPLE 6

100 g dodecyl oleate (purified by aluminium-oxide treatment) was heated to 100° C. 50 ppm of ([1,3-bis(2,4,6-trimethylphenyl)-2-imidazolidinyliden]dichloro[(2-isopropoxy)(5-trifluoracetamido)benzyliden]]ruthenium(II)) was dissolved in 1 ml toluene, and this was added to the dodecyl oleate.

After 30 seconds the reaction equilibrium conversion was reached. The reaction mixture contained 54.5% dodecyl oleate, 8.8% 9-octadecene and 36.7% 9-octadecenedioic acid di-dodecyl ester. A catalyst efficiency value of 25 was achieved.

COMPARATIVE EXAMPLE

A comparative prior art catalyst as disclosed in US 2011/0171147 was also tested. 100 ml methyl oleate (purified by aluminium-oxide treatment) was heated to 100° C. 250 ppm of ([1,3-bis(2,4,6-trimethylphenyl)-2-imidazolidnyliden]-[2-[[(4-methylphenyl)imino]methyl]-4-nitrophenol]-[3-phenyl-1H-inden-1-ylidene]ruthenium(II)chlorid) was dissolved in 1 ml toluene, and this was added to the methyl oleate.

After 2 hours 30% conversion was obtained, and after 6.5 hours 40.8% conversion was reached. The reaction mixture contained 20.6% dimethyldiester and 20.2% 9-octadecene. A catalyst efficiency value in excess of 97,500 was found with the prior art catalyst.

EXAMPLES 7 TO 9

A number of examples were conducted using catalyst enhancer compounds (Ti(O$^i$Pr)$_4$) and BF$_3$. The starting material was also treated with an antioxidant (TBHQ). The results are shown in Table 1.

TABLE 1

|  | Example 7 | Example 8 | Example 9 |
| --- | --- | --- | --- |
| Methyl Oleate (g) | 50 | 50 | 50 |
| Catalyst (ppm) | 5 | 3 | 5 |
| Ti(O$^i$Pr)$_4$ (ppm) | 200 | 200 | 0 |
| BF$_3$ (ppm) | 0 | 0 | 200 |
| Conversion | 50% | 46% | 41% |

Catalyst used was ([1,3-bis(2,4,6-trimethylphenyl)-2-imidazolidinyliden]dichloro[(2-isopropoxy)(5-isobutoxyacetamido)benzyliden]]ruthenium(II)).

Improvements were seen on addition of catalyst enhancer compound. In Example 8 addition of 200 ppm gave 50% conversion whilst using only 5 ppm of catalyst. Example 8 used lower concentration of catalyst (3 ppm) which resulted in 46% conversion. Example 9 shows use of BF$_3$ as another catalyst enhancer compound with similar results.

It is to be understood that the invention is not to be limited to the details of the above embodiments, which are described by way of example only. Many variations are possible.

The invention claimed is:
1. A self-metathesis process for the production of unsaturated dicarboxylic acids and/or unsaturated dicarboxylic acid diesters, wherein unsaturated fatty acids and/or esters of unsaturated fatty acids are reacted in the presence of at least one catalyst compound of Formula (I):

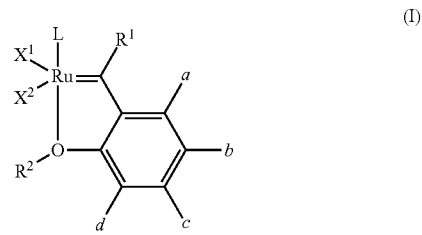

wherein
L represents a neutral ligand;
R$^1$ represents hydrogen, C$_1$ to C$_6$ alkyl, C$_2$ to C$_6$ alkenyl, C$_2$ to C$_6$ alkynyl, C$_5$ or C$_6$ aryl, aralkyl, hydroxyl, C$_1$ to C$_6$ alkoxy, aryloxy, or arylalkoxy;
a, b, c, and d each independently represent hydrogen, C$_1$ to C$_6$ alkyl, C$_1$ to C$_6$ alkoxy, C$_5$ or C$_6$ aryl, or an electron withdrawing group;
X$^1$ and X$^2$ each independently represent anionic ligands;

R² represents a C₁ to C₆ alkyl, C₅ or C₆ cycloalkyl, C₅ or C₆ aryl, C₁ to C₆ alkoxy, aryloxy, arylalkoxy, or alkanone;

wherein the reaction is performed in the absence of solvents or in the presence of a solvent consisting of hydrocarbons and/or alcohols, and wherein a catalyst enhancer compound is also present during the reaction, said catalyst enhancer compound being a non-catalyst enhancer that is a titanium based compound.

2. The process according to claim 1 wherein the level of conversion is at least 40 wt. %.

3. The process according to claim 1 wherein the time to reach equilibrium is less than 20 minutes.

4. The process according to claim 1 wherein the concentration of catalyst of Formula (I) is less than 100 ppm.

5. The process according to claim 4 wherein the concentration of catalyst of Formula (I) is less than 10 ppm.

6. The process according to claim 1 wherein the catalyst efficiency is less than 100.

7. The process according to claim 6 wherein the catalyst efficiency is less than 10.

8. The process according to claim 1 wherein the catalyst of Formula (I) retains over 75% of its activity after 30 minutes.

9. The process according to claim 1 wherein no chemical treatment of the feedstock or starting material to remove catalyst poisons is performed.

10. The process according to claim 1 wherein the unsaturated fatty acids and/or esters of unsaturated fatty acids starting material comprises (i) a peroxide level of less than 3 meq/kg, (ii) a water content of less than 0.05 wt %, (iii) a hydroxyl value of less than 0.05 mg(KOH)·g⁻¹, and/or (iv) an acid value of less than 0.10 mg(KOH)·g⁻¹.

11. The process according to claim 1 wherein the non-catalyst enhancer is selected from the group consisting of titanium (IV) methoxide, titanium (IV) ethoxide, titanium (IV) propoxide, titanium (IV) isopropoxide, titanium (IV) butoxide, titanium (IV) tert-butoxide, titanium (IV) 2-ethylhexoxide, titanium (IV) 2-ethyl-1,3-hexanediolate, titanium (IV) tetrachloride, titanium (IV) tetrabromide, titanium (IV) tetrafluoride, titanium (IV) tetraiodide, and mixtures thereof.

12. The process according to claim 1 wherein the concentration of the non-catalyst enhancer is 10 ppm to 1,000 ppm.

13. The process according to claim 1 wherein the catalyst compound is of Formula (I) and is selected from the group consisting of

[1,3-bis(2,6-diisopropylphenyl)-2-imidazolidinylidene] dichloro [2-(1-methylacetoxy) phenyl]methyleneruthenium(II);

[1,3-bis(2,4,6-trimethylphenyl)-2-imidazolidinylidene] dichloro [2-(1-methylacetoxy) phenyl]methyleneruthenium(II);

[1,3-bis(2,6-diisopropylphenyl)-2-imidazolidinylidene] dichloro[[2-(2-oxopropoxy) phenyl]methylene]ruthenium(II);

[1,3-bis(2,4,6-trimethylphenyl)-2-imidazolidinylidene] dichloro[[2-(2-oxopropoxy) phenyl]methylene]ruthenium(II);

([1,3-bis(2,4,6-trimethylphenyl)-2-imidazolidinyliden]dichloro[(2-isopropoxy)(5-trifluoracetamido)benzyliden]]ruthenium(II));

([1,3-bis(2,6-diisopropylphenyl)-2-imidazolidinyliden] dichloro[(2-isopropoxy)(5-trifluoracetamido)benzyliden]]ruthenium(II));

([1,3-bis(2,6-diisopropylphenyl)-2-imidazolidinyliden] dichloro[(2-isopropoxy)(5-isobutoxyacetamido)benzyliden]]ruthenium(II));

([1,3-bis(2,4,6-trimethylphenyl)-2-imidazolidinyliden]dichloro[(2-isopropoxy)(5-isobutoxyacetamido)benzyliden]]ruthenium(II));

([1,3-bis(2,6-diisopropylphenyl)-2-imidazolidinyliden] dichloro[(2-isopropoxy)(5-ethylesteracetamido)benzyliden]]ruthenium(II)); and ((1,3-bis(2,6-diisopropylphenyl)-imidazolidin-2-yliden) ((2-ethyl-3-oxo-3,4,-dihydr-2H-benzo[b][1,4]oxazin-8-yl)methylene)ruthenium(II)chlorid).

14. A process for improving the efficiency of the catalyst compound of Formula (I) in a self-metathesis process for the production of unsaturated dicarboxylic acids and/or unsaturated dicarboxylic acid diesters, wherein unsaturated fatty acids and/or esters of unsaturated fatty acids are reacted in the presence of at least one catalyst compound of Formula (I):

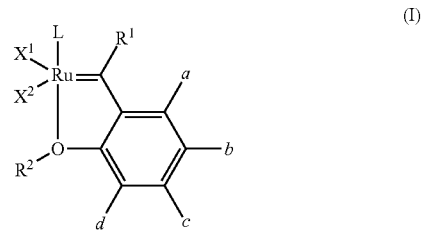

wherein
L represents a neutral ligand that is a carbene ligand;
R¹ represents hydrogen, C₁ to C₆ alkyl, C₂ to C₆ alkenyl, C₂ to C₆ alkynyl, C₅ or C₆ aryl, aralkyl, hydroxyl, C₁ to C₆ alkoxy, aryloxy, or arylalkoxy;
a, b, c, and d each independently represent hydrogen, C₁ to C₆ alkyl, C₁ to C₆ alkoxy, C₅ or C₆ aryl, or an electron withdrawing group;
X¹ and X² each independently represent anionic ligands;
R² represents a C₁ to C₆ alkyl, C₅ or C₆ cycloalkyl, C₅ or C₆ aryl, C₁ to C₆ alkoxy, aryloxy, arylalkoxy, or alkanone;

wherein the process comprises adding a catalyst enhancer to the reaction and wherein the reaction is performed in the absence of solvents or in a solvent consisting of hydrocarbons and/or alcohols.

15. The process according to claim 1, wherein L represents a carbene ligand.

* * * * *